United States Patent [19]

Beneyto

[11] Patent Number: 5,173,329
[45] Date of Patent: Dec. 22, 1992

[54] PROCESS FOR CREATING MAGNETIC IMPRESSIONS ON SHEETLIKE MATERIAL

[76] Inventor: Eduardo M. Beneyto, Burriana Street No. 36, Valencia, Spain

[21] Appl. No.: 605,791

[22] Filed: Oct. 26, 1990

[30] Foreign Application Priority Data

Oct. 26, 1989 [ES] Spain .................................. 8903616

[51] Int. Cl.⁵ .............................................. B05D 3/14
[52] U.S. Cl. .................................... 427/547; 427/128; 427/130; 427/131; 427/177; 427/261; 427/265; 427/378; 427/385.5; 427/407.1; 427/419.5
[58] Field of Search ............... 427/419.5, 385.5, 407.1, 427/127-132, 47, 177, 261, 265, 378; 428/900, 694, 695

*Primary Examiner*—Bernard Pianalto
*Attorney, Agent, or Firm*—Flynn, Thiel, Boutell & Tanis

[57] ABSTRACT

A process with its corresponding device for the obtainment of a laminar body with therapeutic aims. The laminar body is provided with a first magnetizable impression in the form of a mesh pattern, and a second impression of bipolar geometric form and created of magnetite-rich ink is formed as a core within each ring which makes up the mesh. The impressions are magnetized by displacing the laminar body through the air gap of a magnetizer. Polymerizing and fixing of the resin incorporated in the ink occurs by displacing the laminar body across a forced air heater, followed by gathering of the marked and polymerized laminar body onto a bobbin which determines the linear velocity of the laminar body.

5 Claims, 2 Drawing Sheets

PROCESS FOR CREATING MAGNETIC IMPRESSIONS ON SHEETLIKE MATERIAL

FIELD OF THE INVENTION

The present invention relates to a process with its corresponding device for the obtainment of a laminar body with therapeutic aims.

BACKGROUND OF THE INVENTION

More specifically, the invention constitutes an improvement of the subject of Spanish Patent No. 8802257 of the same applicant relating to a process for the obtainment of bodies and materials intended for the creation and attainment of magnetic fields usable in clinical and therapeutic applications, and deals with magnetic fields applied to a magnetite-rich ink printed in the form of a continuous mesh pattern on laminar bodies.

SUMMARY OF THE INVENTION

The present invention deals with furnishing the flexible laminar (i.e. a sheetlike cloth) body with a second impression of bipolar geometric form, the function of which is to produce magnetic fields with better adjustment potential than those already obtained and transported by the continuous mesh and which, on being subjected as a whole to a magnetizer, furnishes a greater potential of the magnetic field and therefore greater curative powers in applications of magnetotherapy.

This second impression takes on a rectangular, quadrangular, compass needle shaped, etc. geometrical form, printed on respective closed spaces defined by the continuous meshes printed in the earlier marking and which act in the manner of magnetic dipoles.

With the system which is the subject of the present invention, it is succeeded in improving the control of the intensity of the magnetic field using the following methods:

a) distance of the laminar body to be magnetized from the magnetic core created by the magnetizer, b) thickness of the deposited layer of magnetic substance, c) specific provision of magnetic substance employed in the manufacture of the marking ink, d) variation of the relative velocity of the marked body with respect to the magnetizer, e) variation of the relative position of the magnetizer with respect to the marked body.

BRIEF DESCRIPTION OF THE DRAWINGS

With the aim of facilitating the explanation, the present descriptive document is accompanied by some pages of drawings in which one embodiment has been shown and which is cited by way of example.

In the drawings.

DETAILED DESCRIPTION

Figure 1:
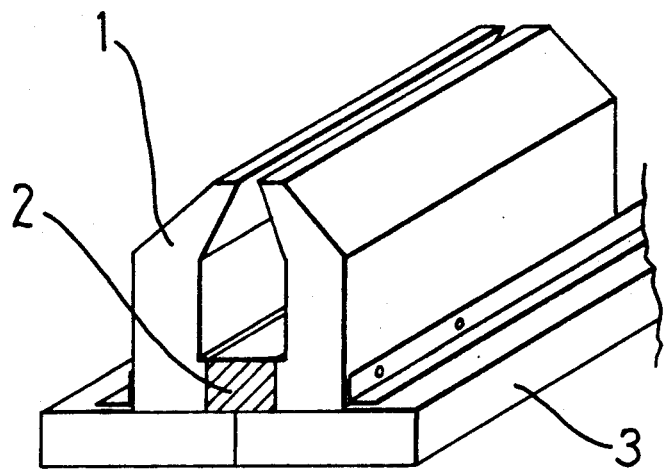
FIG. 1 shows a perspective view of a magnetizer anchored to a base.
Figure 2:
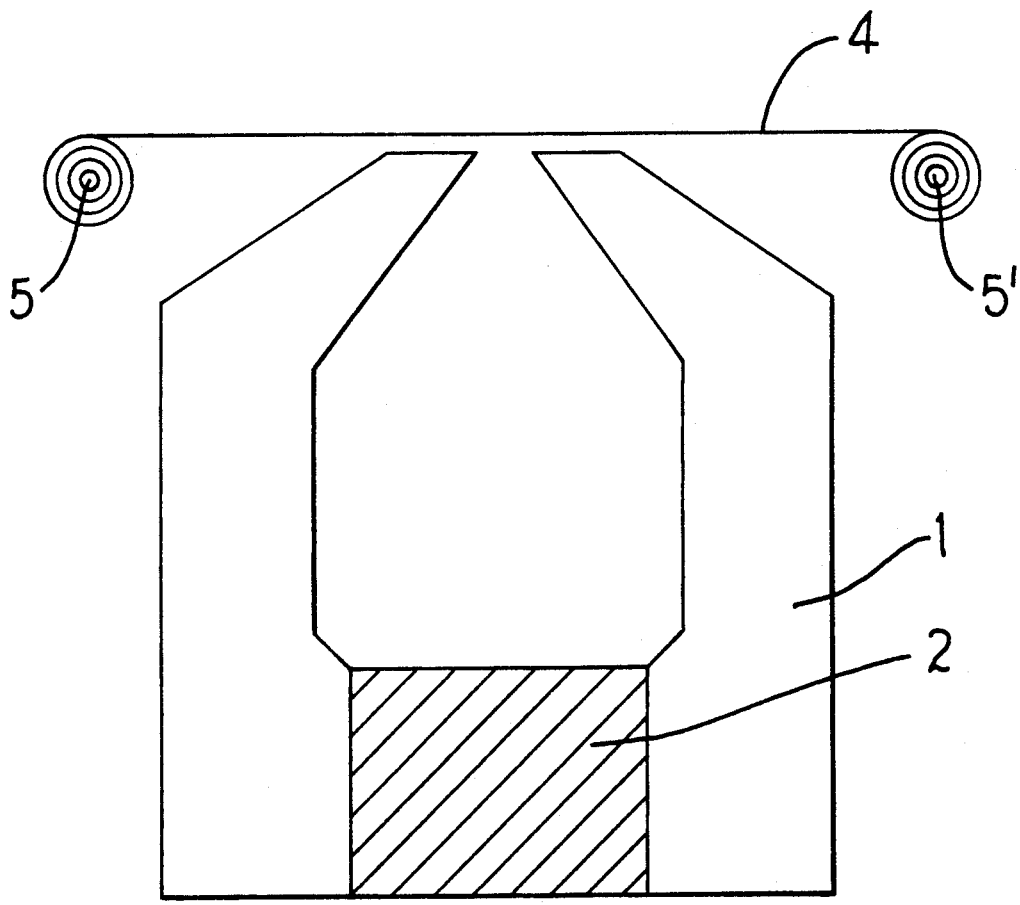
FIG. 2 corresponds to a view in elevation of the magnetizer of FIG. 1, magnetizing a laminar body which passes by between bobbins.
Figure 3:
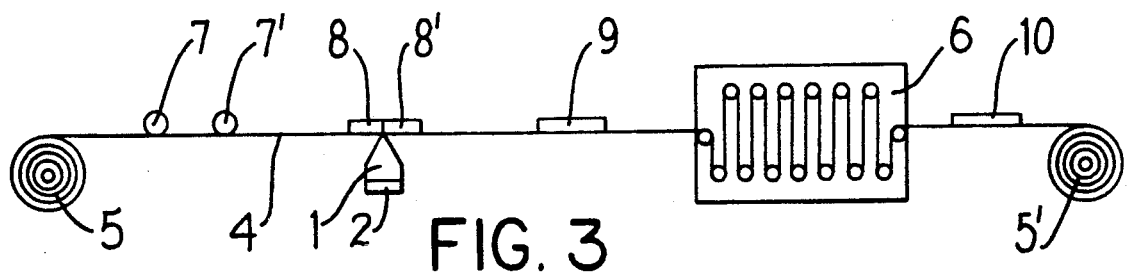
FIGS. 3 and 4 show schematically two alternatives of the procedure for marking and magnetizing a laminar body.
Figure 4:
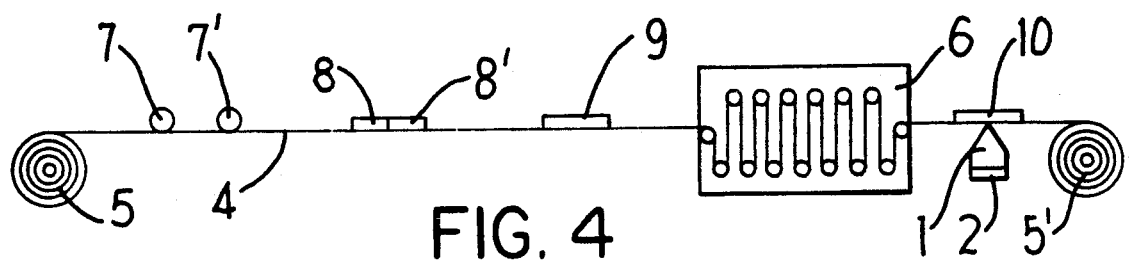

Referring to the figures, in the embodiment thereof is seen a magnetizer consisting of a parallelepipedal body longitudinally slotted above, consisting of wrought iron 1, except for the base which is a permanent magnet 2, with the aim of generating the magnetic flux to be transmitted and concentrating it in the air gap. Such magnetizers make up modules of defined dimensions, which can be arranged in series, using connections and anchorage to a base 3, with the aim of increasing the length of the air gap depending on the width of the printed body to be magnetized. The printed body includes a flexible sheetlike body 4, such as a woven fabric. The latter passes between two bobbins 5 and 5', between which is located the magnetizer, the air gap of which magnetizer magnetizes the ink printed on the body 4 which is presented to it.

The marking and magnetizing process consists in arranging the laminar body 4 which passes by in a straight line between two bobbins 5 and 5' and which, proceeding from the bobbin 5 of unmarked material, is subjected to the printing action of marking cylinders 7 and 7', which produce in it respective impressions 8 and 8' of magnetite-rich ink which, after passing through the air gap of the magnetizer, enter, with the wet unpolymerized ink 9, a forced air heater 6, which polymerizes and fixes the resin incorporated in the ink, exiting from same marked and polymerized 10, so as to be gathered on the bobbin 5' which determines the linear velocity of the laminar body.

Similarly, a variant has been provided consisting in the arrangement of the magnetizer after the air heater 6, magnetizing the ink once it has been marked and polymerized.

Figure 5:
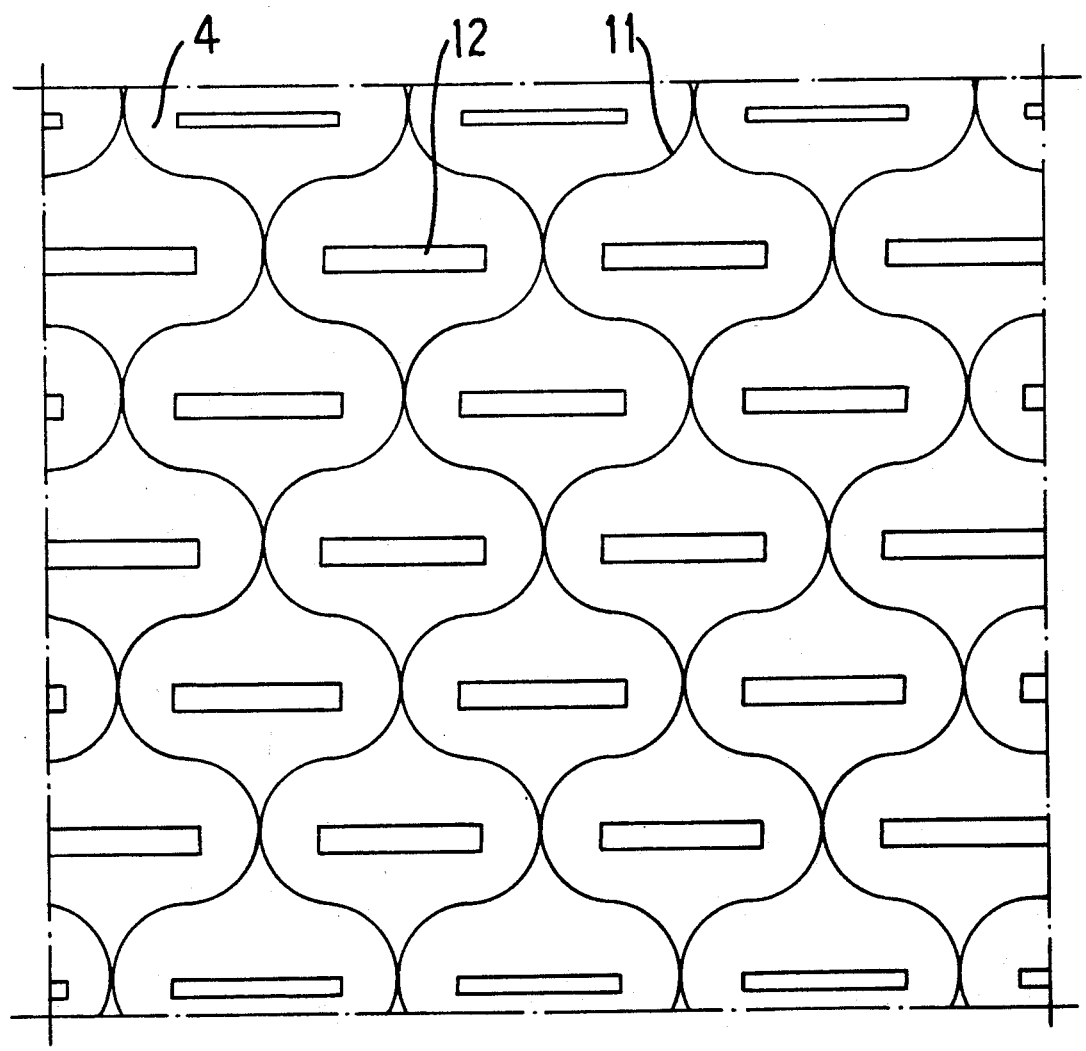
FIG. 5 shows a detail, in plan view, of a laminar body with the two impressions which make up the whole of the magnetizable marking which is the subject of the present invention.

FIG. 5 shows both types of ink respectively designated as 11 and 12 printed on the laminar body 4, namely the ink defining the continuous mesh configuration 11, and the ink defining the secondary rectangular-shaped impressions 12 which are arranged within the spaces defined by the loops or meshes.

In the following, the composition of both inks is set out. The meshes 11 are created by the roller 7, whereas the impressions 12 are created by roller 7'.

Composition of the ink which makes up the mesh 11:

18.05% water, for the attainment of homogenization of products; 21.85% magnetite powders as premagnetized magnetic powder of the PO2-F type; 10.00% metal powders for the attainment of the electrostatic sealing, composed of 94% copper, 4% zinc, 1% bronze, 1% aluminum, with a grain size of 7 to 8 microns; 0.93% Cresaclear (white spirit—trade designation for a commercially available agent for controlling viscosity) as a synthetic thickener; 0.23% ammonia for the attainment of alkalinity for enhancing the pH of the thickener; 0.31% triethanolamine as stabilizer for the marking paste or ink; 45.12% SR binder (trade designation for a commercially available binder using a petroleum based carrier for maintaining adequate thixotropy) containing acrylic resin with 45% solids for the anchoring of the ink to the fabric; 2.34% MF adhesive (trade designation for a commercially available adhesive fixer) for the attainment of resistance to rubbing for washing; and 1.17% Rollerblock (trademark of a commercially available compound containing lubricants such as linseed oil and mineral oil dispersed in white spirit or similar) so as to temper and not block the wefts and meshes of the marking and improve the impression.

Composition of the ink which makes up the magnetic core 12:

18.05% water for the attainment of homogenization of products; 31.85% premagnetized magnetic powders of the PO2-F type; 0.93% Cresaclear as a synthetic thickener; 0.23% ammonia for the attainment of alkalinity for enhancing the pH of the thickener; 0.31% triethanolamine as stabilizer for the marking paste or ink; 45.12% SR binder as acrylic resin with 45% solids for the anchoring of the ink to the fabric; 2.34% MF adhesive, for the attainment of resistance to rubbing for washing; and 1.17% Rollerblock so as to temper and not block the sections and meshes of the marking and improving the impression.

Similarly, variants have been provided with respect to the earlier formulation, which differ from the same in the percentage variation of magnetite powders and water with the aim of varying the magnetizing potential. The proportion is 40% magnetite and 9.90% water in one variant and 49.90% magnetite without water in the other variant.

In its essentials, the invention can be put into practice in other embodiments which differ in detail from that indicated by way of example in the description and to which the protection which is applied for will likewise extend. Thus it will be possible to embody it in other forms and with the most suitable materials so that everything thereof remains included within the spirit of the claims.

The embodiments of the invention in which an exclusive property or privilege is claimed are defined as follows:

1. In a process for producing a sheetlike body having a magnetic field associated therewith, including the steps of providing a sheetlike body, and applying to a surface of the sheetlike body a first magnetizable impression in the form of a meshlike pattern, said first impression being formed by a first magnetite-rich ink having a resin incorporated therein, said meshlike pattern including a plurality of closed rings disposed in adjoining relationship on the surface of the sheetlike body, each of the closed rings defining thereinside a respective portion of the surface of the sheetlike body, the improvement comprising the further steps of:

transporting the sheetlike body at a displacement velocity in a displacement direction, including drivingly winding the sheetlike body onto a first bobbin while simultaneously unwinding the sheetlike body from a second bobbin;

applying a plurality of second magnetizable impressions to the respective portions of the surface and generally centrally with the respective rings following the application of the first magnetizable impression, each of the second impressions having a bipolar geometric shape and being formed by a second magnetite-rich ink having a resin incorporated therein;

magnetizing the second impressions by displacing the sheetlike body at the displacement velocity through an air gap of a magnetizer; and polymerizing and fixing the resin in the ink by displacing the sheetlike body at the displacement velocity across a forced air heater.

2. The process according to claim 1, including the further steps of providing the magnetizer with a generally parallelepipedal body including a wrought iron upper portion and a base which is a permanent magnet, providing the wrought iron upper portion with a substantially linear, upwardly opening slot which defines the air gap, and generating, by means of the permanent magnet, a magnetic flux which is concentrated in the air gap.

3. The process according to claim 1, including the further step of positioning the air heater and the magnetizer in succession relative to the displacement direction of the sheetlike body so that the ink is magnetized after it has been polymerized.

4. The process according to claim 1, including the further steps of magnetizing the first impression simultaneously with the second impressions, and polymerizing the resin in the first impression simultaneously with the resin in the second impressions.

5. The process according to claim 1, wherein the sheetlike body has a laminar construction.

* * * * *